United States Patent [19]
Lupon-Roses et al.

[11] Patent Number: 5,872,125
[45] Date of Patent: Feb. 16, 1999

[54] POLYMORPHS OF LESOPITRON DIHYDROCHLORIDE AND ITS HYDRATED FORMS, PREPARATION PROCESSES AND COMPOSITIONS CONTAINING IT

[75] Inventors: Pilar Lupon-Roses; Jaime Tomas-Navarro; Salvador Puig-Torres; Jordi Frigola-Constansa, all of Barcelona, Spain

[73] Assignee: Laboratorios Del Dr. Esteve, S.A., Barcelona, Spain

[21] Appl. No.: 776,113

[22] PCT Filed: May 29, 1996

[86] PCT No.: PCT/ES96/00121

§ 371 Date: Jan. 21, 1997

§ 102(e) Date: Jan. 21, 1997

[87] PCT Pub. No.: WO96/38439

PCT Pub. Date: Dec. 5, 1996

[30] Foreign Application Priority Data

May 31, 1995 [ES] Spain ................................ P 9501086

[51] Int. Cl.[6] ...................... C07D 403/14; C07D 403/02; A61K 31/495; A61K 31/505
[52] U.S. Cl. ............................................ 514/269; 544/295
[58] Field of Search .............................. 544/295; 514/269

[56] References Cited

U.S. PATENT DOCUMENTS

| | | | |
|---|---|---|---|
| 5,128,343 | 7/1992 | Pinol et al. | 514/252 |
| 5,162,323 | 11/1992 | Frigola-Constansa et al. | 514/252 |
| 5,182,281 | 1/1993 | Frigola-Constansa et al. | 514/252 |
| 5,536,836 | 7/1996 | Merce-Vidal et al. | 544/295 |

FOREIGN PATENT DOCUMENTS

| | | |
|---|---|---|
| 0382637 | 8/1990 | European Pat. Off. . |
| 0429360 | 5/1991 | European Pat. Off. . |
| 0497658 | 8/1992 | European Pat. Off. . |
| 0497659 | 8/1992 | European Pat. Off. . |
| 0502786 | 9/1992 | European Pat. Off. . |

*Primary Examiner*—Matthew V. Grumbling
*Attorney, Agent, or Firm*—Ladas & Parry

[57] ABSTRACT

It comprises the new polymorphs I and II of Lesopitron dihydrochloride, characterized by their infrared spectra and their X-ray diffraction patterns. They are obtained by crystallization of Lesopitron dihydrochloride. It also comprises the forms I-hydrate and II-hydrate, which are obtained from the corresponding polymorphs, which have a water content from 3 to 6% and from 1.5 to 2.5%, respectively. These products are used in human medicine mainly due to their pharmacological activity over the central nervous system.

19 Claims, 8 Drawing Sheets

POLYMORPHS OF LESOPITRON DIHYDROCHLORIDE AND ITS HYDRATED FORMS, PREPARATION PROCESSES AND COMPOSITIONS CONTAINING IT

FIELD OF THE INVENTION

The present invention relates to new polymorphs of the dihydrochloride of 2-[4-[4-[4-(chloropyrazole-1-yl) butyl]-1-pyperazinyl] pyrimidine ("Lesopitron" dihydrochloride), and to its hydrated forms, to processes for its preparation and to compositions which contain them.

BACKGROUND TO THE INVENTION

The invention relates to the pyrimidinic compound 2-[4-[4-[4-(chloropyrazole-1-yl) butyl]-1-pyperazinyl] pyrimidine, which has the following structural formula:

generically termed Lesopitron, which exhibits pharmacological activity over the central nervous system, particularly an anxiolytic, tranquilizing and antidepressant activity. It can also be used in the treatment of dyskinesias, Parkinsonism and drug induced psychoses, in the treatment of cognitive functions, inhibition of the withdrawal symptoms, and in treatment vomit and gastric secretion related problems.

The synthesis of the compound and an account of its therapeutical properties are described in patents EP 382637B1, EP 429360B1, EP 497658A1 and FR 9314102.

Lesopitron dihydrochloride is particularly important in that it allows for the Lesopitron to be conveniently formulated, for instance, in tablets for oral administration. Therefore, there is the need to produce Lesopitron dihydrochloride in pure and crystalline form, in order to comply with the pharmaceutical requirements and specifications. The patent EP 382637B1 describes a process for the preparation of Lesopitron dihydrochloride.

From the point of view of its application for pharmaceutical use, it was important to obtain, at least, a single crystalline form of Lesopitron dihydrochloride which could be manufactured, stored and formulated without losing the required specifications of a pure pharmaceutical product. During the preparation of samples of Lesopitron dihydrochloride, it was observed that said samples did not meet a unique criterion with respect to their infrared spectrum. A closer study resulted in the unexpected discovery that the corresponding differences were not associated to impurities, but to the existence of a phenomenon of polymorphism. The authors of the present invention have discovered that, depending on the crystallization conditions of the samples of Lesopitron dihydrochloride, different crystalline forms are obtained, observing that they differ not only in their infrared spectrum but in their X-ray diffraction patterns as well.

DETAILED DESCRIPTION OF THE INVENTION

The authors of the present invention have discovered the existence of two polymorphs of Lesopitron dihydrochloride, denominated polymorphs I and II.

Figure 1A:
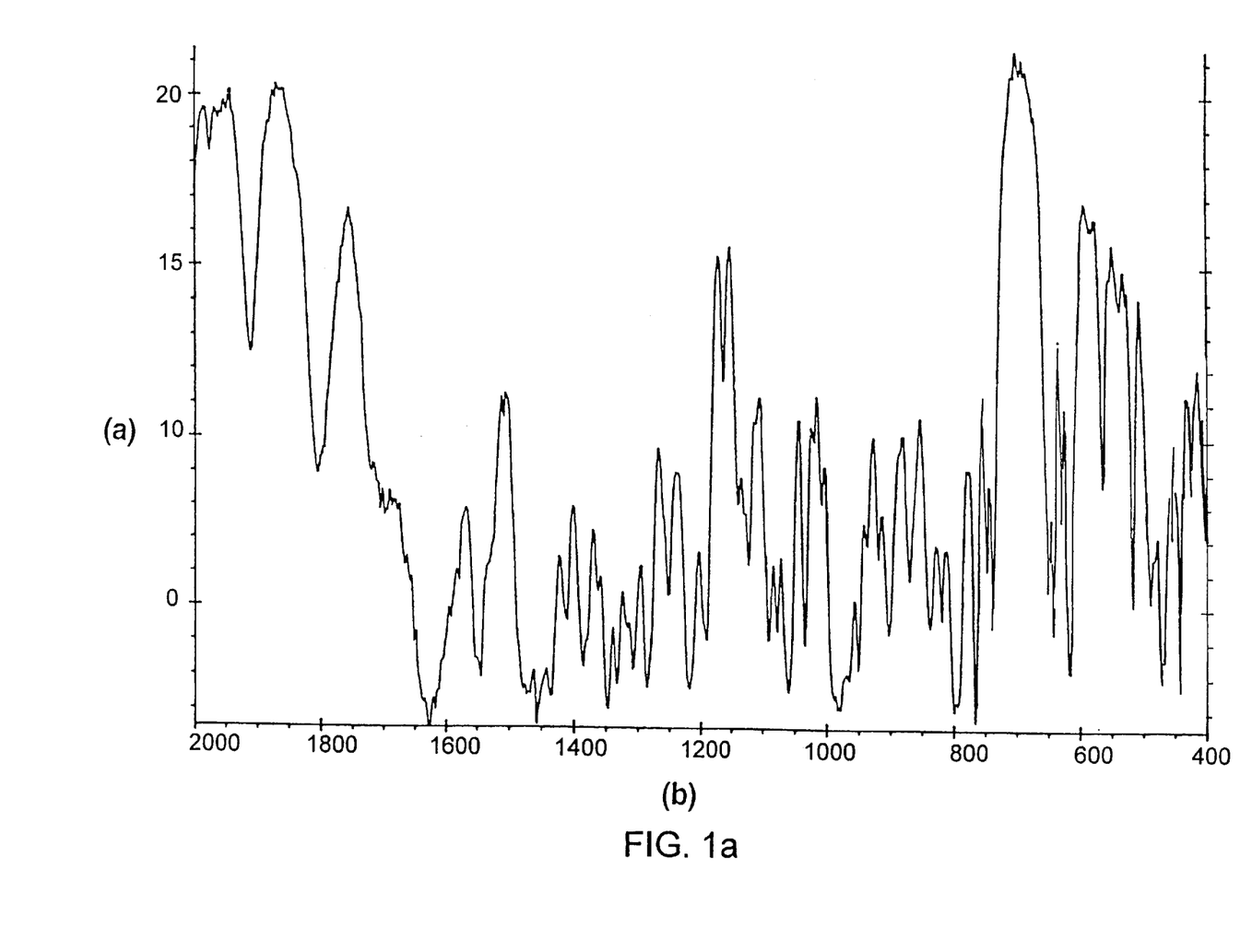
FIG. 1a shows the infrared diffuse reflectance spectrum of polymorph I of Lesopitron dihydrochloride. In this figure (a) indicates percentage transmission and (b) the wavenumber $(cm^{-1})$.

Indeed, the present invention describes a polymorph I of Lesopitron dihydrochloride, characterized by its infrared diffuse reflectance spectrum, which has the following major bands $(cm^{-1})$ (see FIG. 1a):

| | |
|---|---|
| 1910 | 965 |
| 1804 | 950 |
| 1626 | 936 |
| 1544 | 918 |
| 1411 | 902 |
| 1251 | 869 |
| 1218 | 798 |
| 1190 | 793 |
| 1139 | 765 |
| 1129 | 748 |
| 1122 | 738 |
| 1089 | 651 |
| 1077 | 642 |
| 1059 | 629 |
| 1034 | 616 |
| 1019 | 564 |
| 1008 | 518 |
| 988 | 471 |
| 981 | 442 |
| 978 | |

Figure 1B:
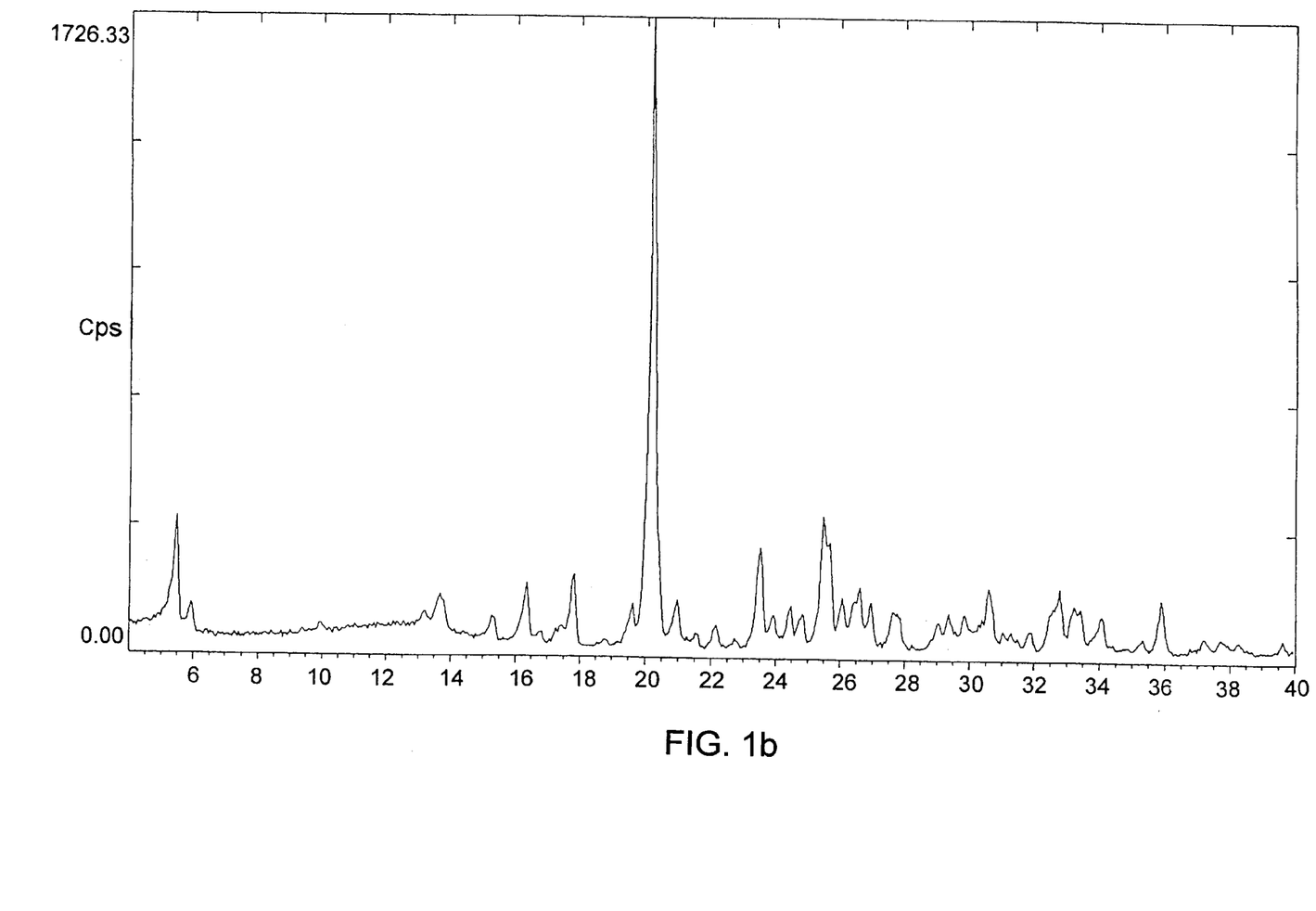
FIG. 1b shows the X-ray powder diffraction spectrum of polymorph I of Lesopitron dihydrochloride, obtained at $\lambda=1.5418$ Å, using a radiation source of $CuK_\alpha$, 40 kV and 30 mA (Siemens D-500 equipment).

Polymorph I is also characterized by the following X-ray powder diffraction spectrum, where d is the spacing and $I/I_o$ is the relative intensity at $\lambda=1.5418$ Å, using a radiation source of $CuK_\alpha$, 40 kV and 30 mA (Siemens D-500 equipment) (see FIG. 1b):

| d (Å) | I/I$_o$ | d (Å) | I/I$_o$ |
|---|---|---|---|
| 16.15 | 21 | 3.47 | 18 |
| 14.96 | 8 | 3.42 | 9 |
| 6.70 | 7 | 3.37 | 9 |
| 6.47 | 9 | 3.35 | 11 |
| 5.79 | 6 | 3.31 | 9 |
| 5.41 | 11 | 3.22 | 7 |
| 4.98 | 13 | 3.21 | 7 |
| 4.52 | 8 | 3.07 | 6 |
| 4.39 | 100 | 3.04 | 7 |
| 4.34 | 18 | 2.99 | 7 |
| 4.24 | 9 | 2.92 | 11 |
| 3.79 | 17 | 2.75 | 8 |
| 3.72 | 7 | 2.70 | 8 |
| 3.64 | 8 | 2.68 | 7 |
| 3.59 | 7 | 2.63 | 7 |
| 3.49 | 22 | 2.50 | 10 |
|  |  | 2.13 | 8 |

Figure 2A:
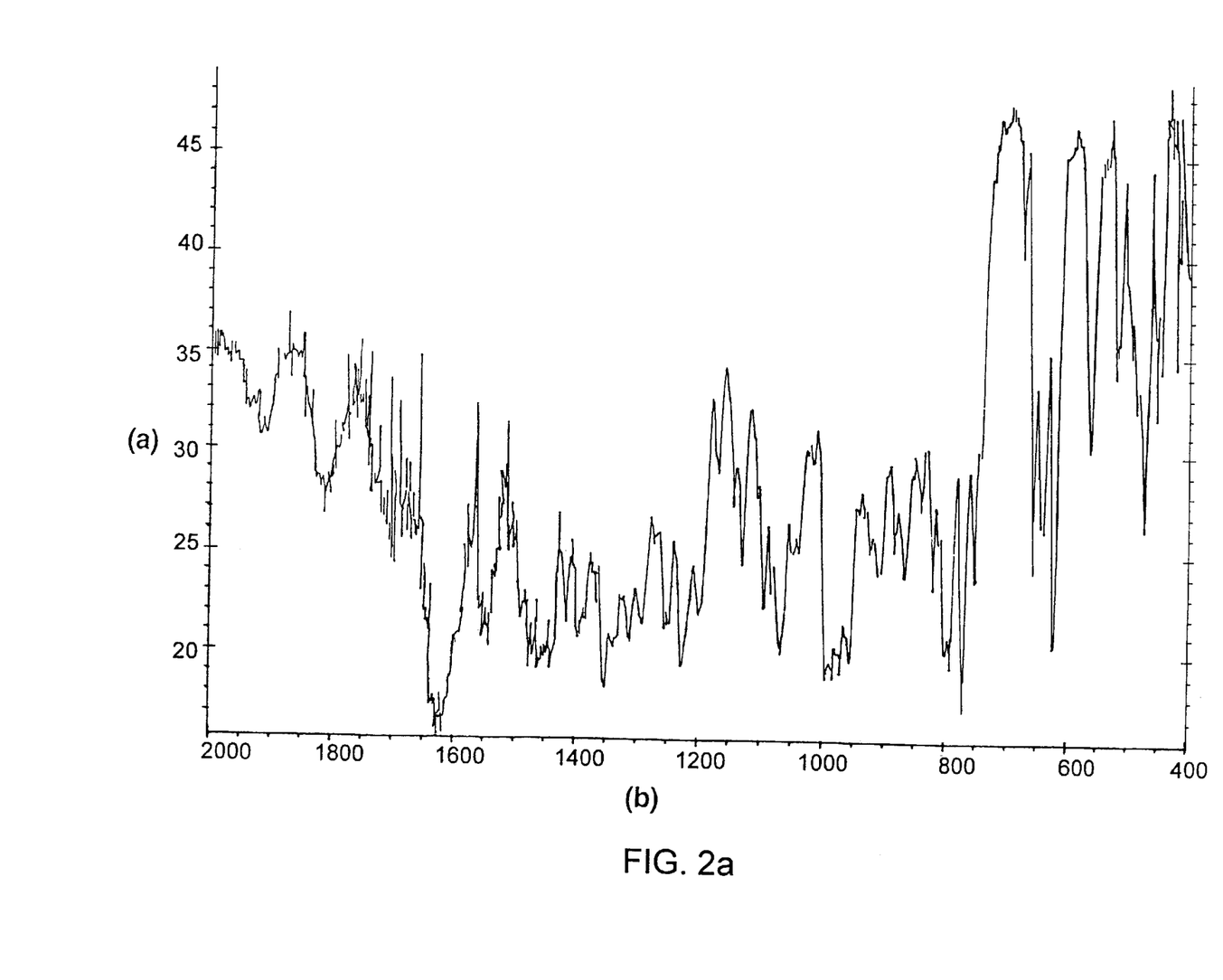
FIG. 2a shows the infrared diffuse reflectance spectrum of polymorph II of Lesopitron dihydrochloride. In this figure (a) indicates percentage transmission and (b) the wavenumber $(cm^{-1})$.

The present invention also describes a polymorph II of Lesopitron dihydrochloride, characterized by its infrared diffuse reflectance spectrum, which has the following major bands (cm$^{-1}$) (see FIG. 2a):

| | |
|---|---|
| 1913 | 989 |
| 1906 | 976 |
| 1799 | 966 |
| 1623 | 952 |
| 1588 | 917 |
| 1544 | 901 |
| 1538 | 878 |
| 1409 | 861 |
| 1248 | 796 |
| 1242 | 789 |
| 1220 | 765 |
| 1195 | 748 |
| 1136 | 651 |
| 1123 | 639 |
| 1085 | 635 |
| 1076 | 618 |
| 1061 | 558 |
| 1041 | 516 |
| 1031 | 510 |
| 1015 | 470 |
| 1011 | |

Figure 2B:
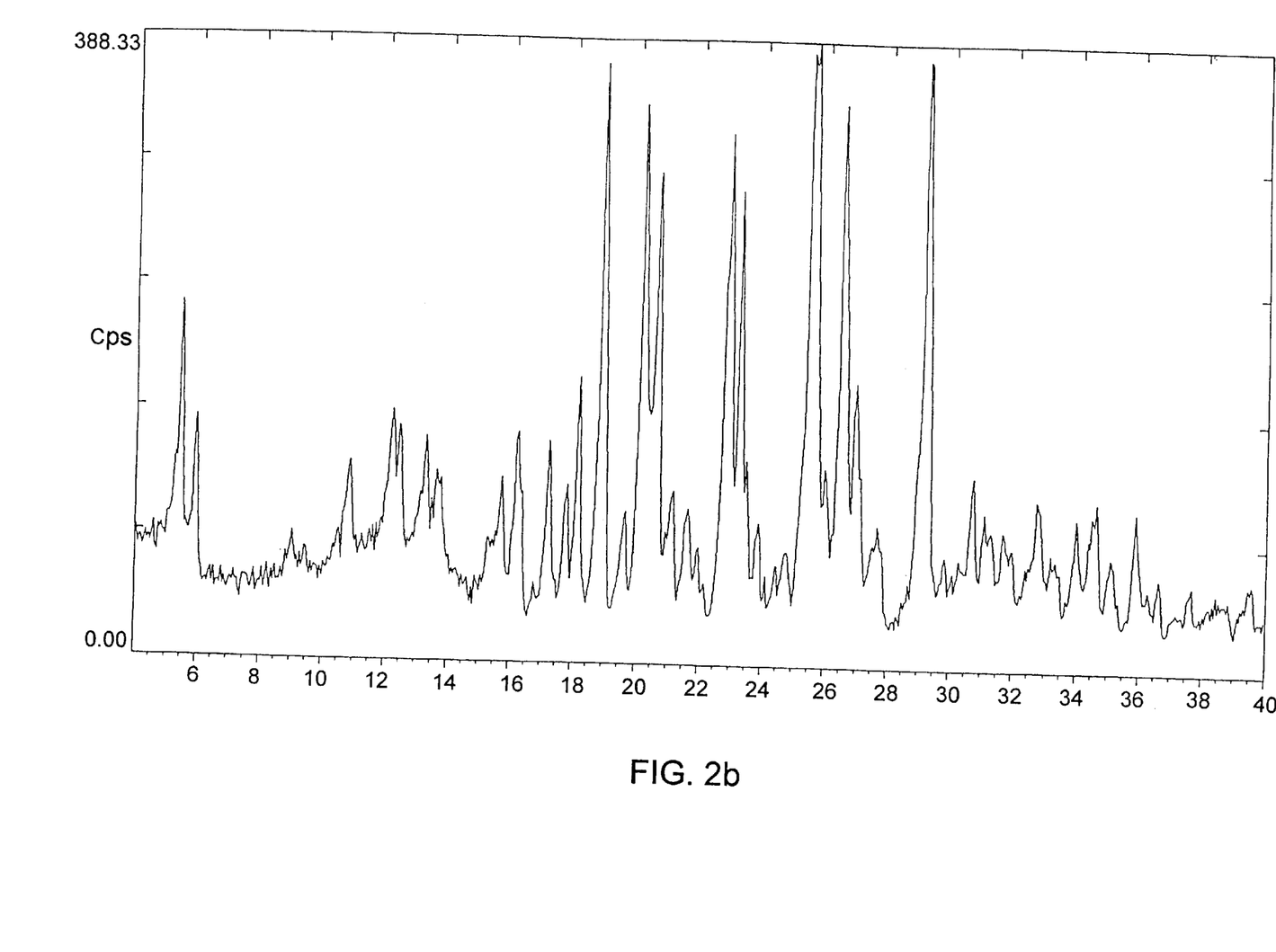
FIG. 2b shows the X-ray powder diffraction spectrum of polymorph II of Lesopitron dihydrochloride, obtained at $\lambda=1.5418$ Å, using a radiation source of $CuK_\alpha$, 40 kV and 30 mA (Siemens D-500 equipment).

Polymorph II is also characterized by the following X-ray powder diffraction spectrum, where d is the spacing and I/I$_o$ is the relative intensity at λ=1.5418 Å, using a radiation source of CuK$_α$, 40 kV and 30 mA (Siemens D-500 equipment) (see FIG. 2b):

| d (Å) | I/I$_o$ | d (Å) | I/I$_o$ |
|---|---|---|---|
| 16.22 | 57 | 4.11 | 25 |
| 14.95 | 38 | 3.90 | 60 |
| 8.15 | 32 | 3.88 | 85 |
| 7.24 | 40 | 3.83 | 76 |
| 7.10 | 37 | 3.78 | 33 |
| 6.68 | 36 | 3.49 | 98 |
| 6.46 | 29 | 3.47 | 100 |
| 5.65 | 29 | 3.42 | 31 |
| 5.45 | 37 | 3.35 | 90 |
| 5.42 | 27 | 3.30 | 45 |
| 5.14 | 35 | 3.05 | 97 |
| 4.98 | 28 | 2.91 | 31 |
| 4.88 | 46 | 2.73 | 27 |
| 4.69 | 96 | 2.63 | 24 |
| 4.39 | 89 | 2.59 | 27 |
| 4.30 | 78 | 2.50 | 25 |
| 4.21 | 28 | 2.13 | 18 |

As it can be observed, the X-ray diffraction patterns and the IR spectra of forms I and II are significantly different, providing great evidence of their individual existence. Therefore, the distinction can be made by means of the infrared spectrum.

The polymorphs I and II claimed in the present invention can be obtained by crystallization, starting from any Lesopitron dihydrochloride, independently of the method of synthesis and its infrared spectrum.

The effect of the cooling rate during the crystallization of warm solutions of Lesopitron dihydrochloride has been studied. It has been found that said rate is the parameter which determines the polymorphic properties of the product obtained.

It has been discovered that a slow cooling rate is most favourable for the production of polymorph I. In contrast, by rapid cooling, polymorph II is obtained.

The solvents used in the crystallizations are 1 to 4 carbon atom aliphatic alcohols, mono or polyhydroxilated, preferably ethanol.

The process claimed for the preparation of the new polymorph I of Lesopitron dihydrochloride, starts from Lesopitron dihydrochloride and is as follows:

(1) Lesopitron dihydrochloride is suspended in a 1 to 4 carbon atom aliphatic alcohol, mono or polyhydroxilated, preferably ethanol. (2) It is warmed under reflux until total solution is achieved, and is kept boiling for 15 minutes. (3) Its is slowly cooled to 50°–55° C., bringing about crystallization. (4) The mass is stirred at 50°–55° C. for 30 minutes. (5) Slow cooling is continued to 0°–5° C., in approximately 2 hours, keeping it for an extra hour at that temperature. (6) The crystalline mass is separated by filtration or centrifugation. (7) The separated product is dried in an air oven at 45° C. for about 15 hours.

Polymorph II is obtained by warming under reflux a suspension of Lesopitron dihydrochloride in a 1 to 4 carbon atom aliphatic alcohol, mono or polyhydroxilated, preferably ethanol. The solution thus obtained is rapidly cooled to 0°–5° C., bringing about crystallization between 20° and 30° C. Subsequently it is separated by filtration and dried in an air oven at 50° C.

It has also been discovered that polymorph I can be prepared from a suspension of polymorph II in a 1 to 4 carbon atom aliphatic alcohol, mono or polyhydroxilated, preferably ethanol, by stirring at a temperature between 25° and 80° C., preferably at 55° C., for a time comprised between 4 and 24 hours, and subsequently cooled to 25° C. in approximately 1 hour.

Another object of the present invention are the hydrated forms of each of the polymorphs, I and II, of Lesopitron dihydrochloride. Said hydrated compounds, termed I-hydrate and II-hydrate, have a different water content. The I-hydrate has a water content between 3 and 6%, whereas the II-hydrate has between 1.5 and 2.5%. Both products have been identified by their corresponding IR and X-ray spectra, clearly demonstrating that they have different crystalline structures.

Figure 3A:
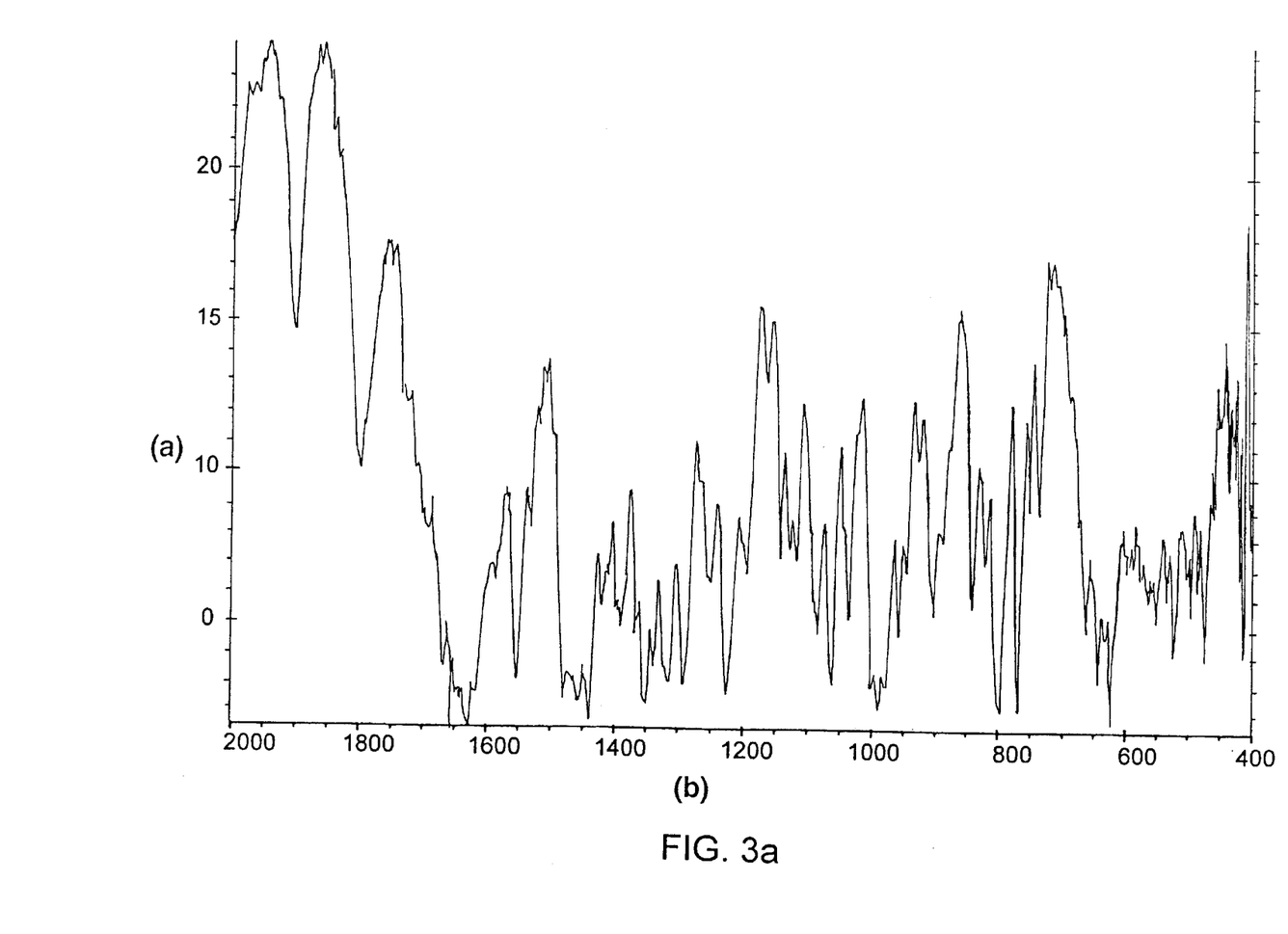
FIG. 3a shows the infrared diffuse reflectance spectrum of the hydrated crystalline form of Lesopitron dihydrochloride, termed I-hydrate. In this figure (a) indicates percentage transmission and (b) the wavenumber $(cm^{-1})$.

The present invention claims a crystalline hydrated form of Lesopitron dihydrochloride, termed I-hydrate, obtained from polymorph I of Lesopitron dihydrochloride, characterized by its infrared diffuse reflectance spectrum which has the following major bands (cm$^{-1}$) (see FIG. 3a):

| | |
|---|---|
| 1900 | 994 |
| 1797 | 983 |
| 1624 | 972 |
| 1548 | 952 |
| 1527 | 940 |
| 1415 | 921 |
| 1404 | 898 |
| 1249 | 883 |
| 1245 | 795 |
| 1220 | 765 |
| 1195 | 749 |
| 1189 | 736 |
| 1139 | 659 |
| 1123 | 641 |
| 1112 | 631 |
| 1084 | 619 |
| 1078 | 520 |
| 1057 | 471 |
| 1031 | 416 |

Figure 3B:
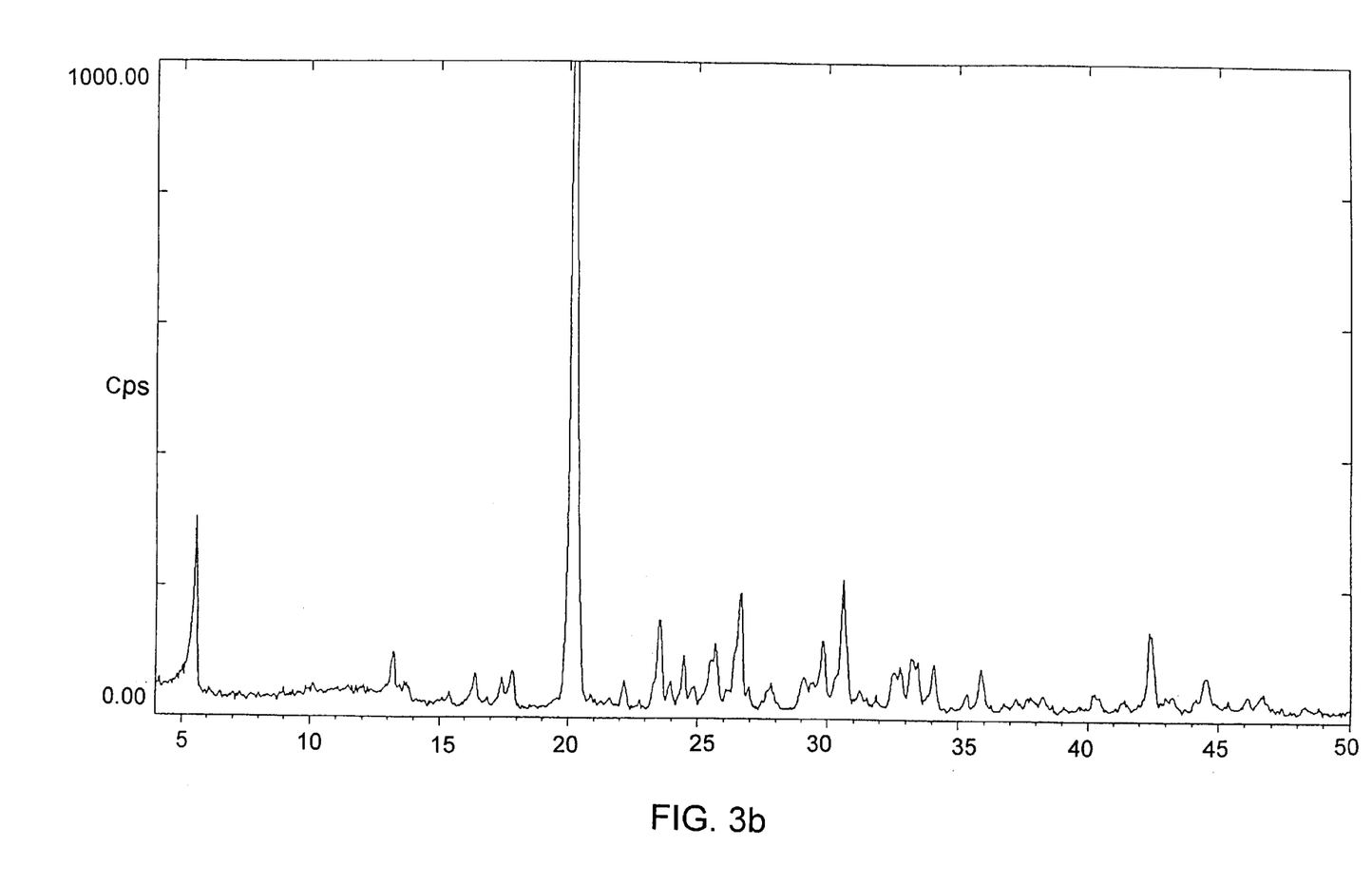
FIG. 3b shows the X-ray powder diffraction spectrum of the hydrated crystalline form of Lesopitron dihydrochloride, termed I-hydrate, obtained at $\lambda=1.5418$ Å, using a radiation source of $CuK_\alpha$, 40 kV and 30 mA (Siemens D-500 equipment).

The I-hydrate compound is also characterized by the following X-ray powder diffraction spectrum, where d is the spacing and $I/I_o$ is the relative intensity at $\lambda=1.5418$ Å, using a radiation source of $CuK_\alpha$, 40 kV and 30 mA (Siemens D-500 equipment) (see FIG. 3b):

| d (Å) | $I/I_o$ | d (Å) | $I/I_o$ |
|---|---|---|---|
| 15.98 | 15 | 3.40 | 2 |
| 8.75 | 2 | 3.37 | 5 |
| 6.71 | 5 | 3.35 | 9 |
| 6.46 | 2 | 3.31 | 2 |
| 5.77 | 2 | 3.21 | 3 |
| 5.41 | 3 | 3.07 | 3 |
| 4.98 | 3 | 3.03 | 2 |
| 4.38 | 100 | 2.99 | 6 |
| 4.01 | 3 | 2.92 | 10 |
| 3.81 | 3 | 2.75 | 3 |
| 3.77 | 7 | 2.73 | 4 |
| 3.71 | 3 | 2.69 | 4 |
| 3.64 | 5 | 2.68 | 4 |
| 3.58 | 2 | 2.63 | 4 |
| 3.49 | 4 | 2.50 | 4 |
| 3.47 | 5 | 2.13 | 6 |

Figure 4A:
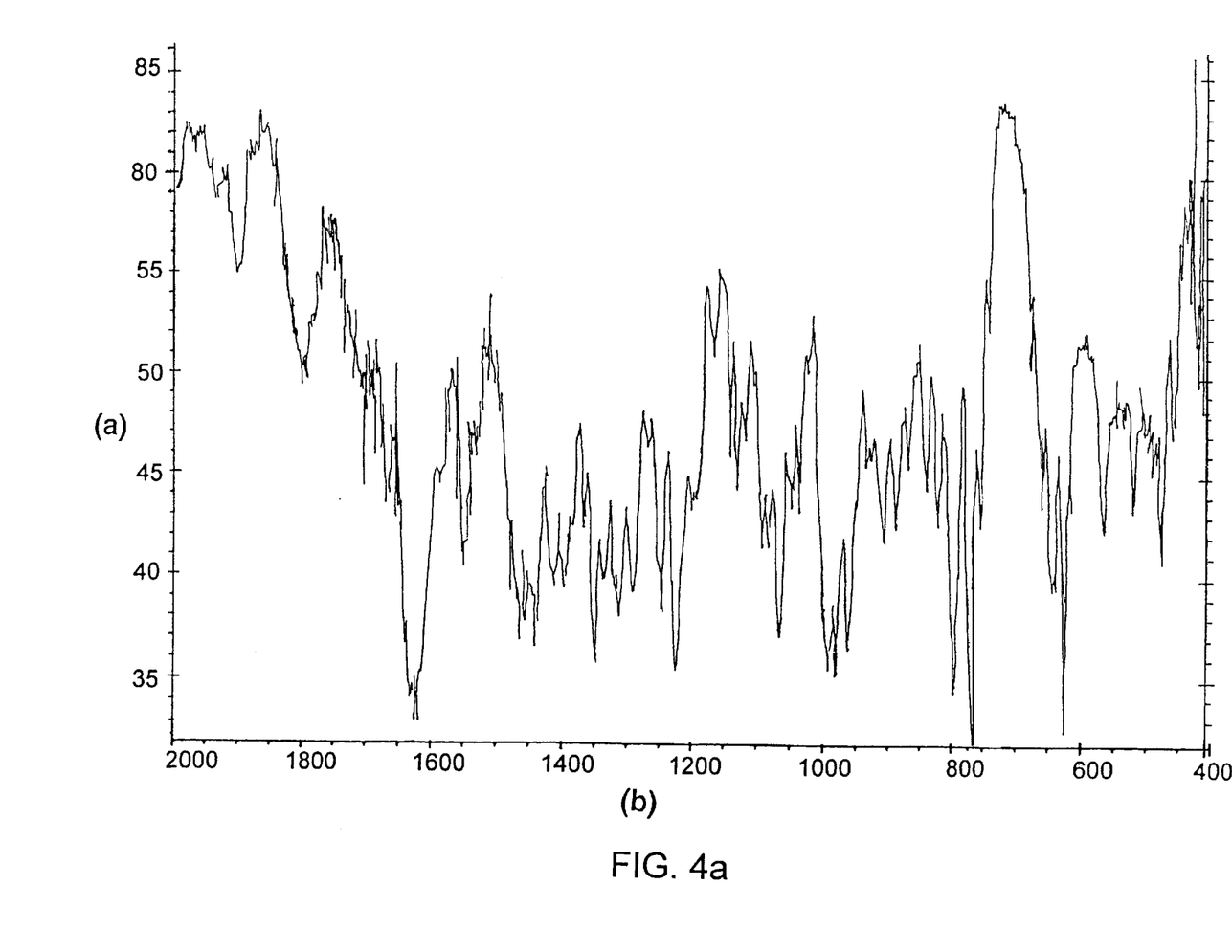
FIG. 4a shows the infrared diffuse reflectance spectrum of the hydrated crystalline form of Lesopitron dihydrochloride, termed II-hydrate. In this figure (a) indicates percentage transmission and (b) the wavenumber $(cm^{-1})$.

The present invention also describes a crystalline hydrated form of Lesopitron dihydrochloride, termed II-hydrate, obtained from polymorph II of Lesopitron dihydrochloride, characterized by its infrared diffuse reflectance spectrum, which has the following major bands (cm$^{-1}$) (see FIG. 4a):

| | |
|---|---|
| 1902 | 971 |
| 1798 | 952 |
| 1621 | 940 |
| 1549 | 925 |
| 1537 | 917 |
| 1411 | 898 |
| 1404 | 881 |
| 1243 | 861 |
| 1219 | 790 |
| 1195 | 765 |
| 1189 | 749 |
| 1137 | 734 |
| 1123 | 659 |
| 1112 | 654 |
| 1087 | 639 |
| 1077 | 634 |
| 1057 | 618 |
| 1041 | 558 |
| 1029 | 517 |
| 1016 | 512 |
| 994 | 470 |
| 985 | |

Figure 4B:
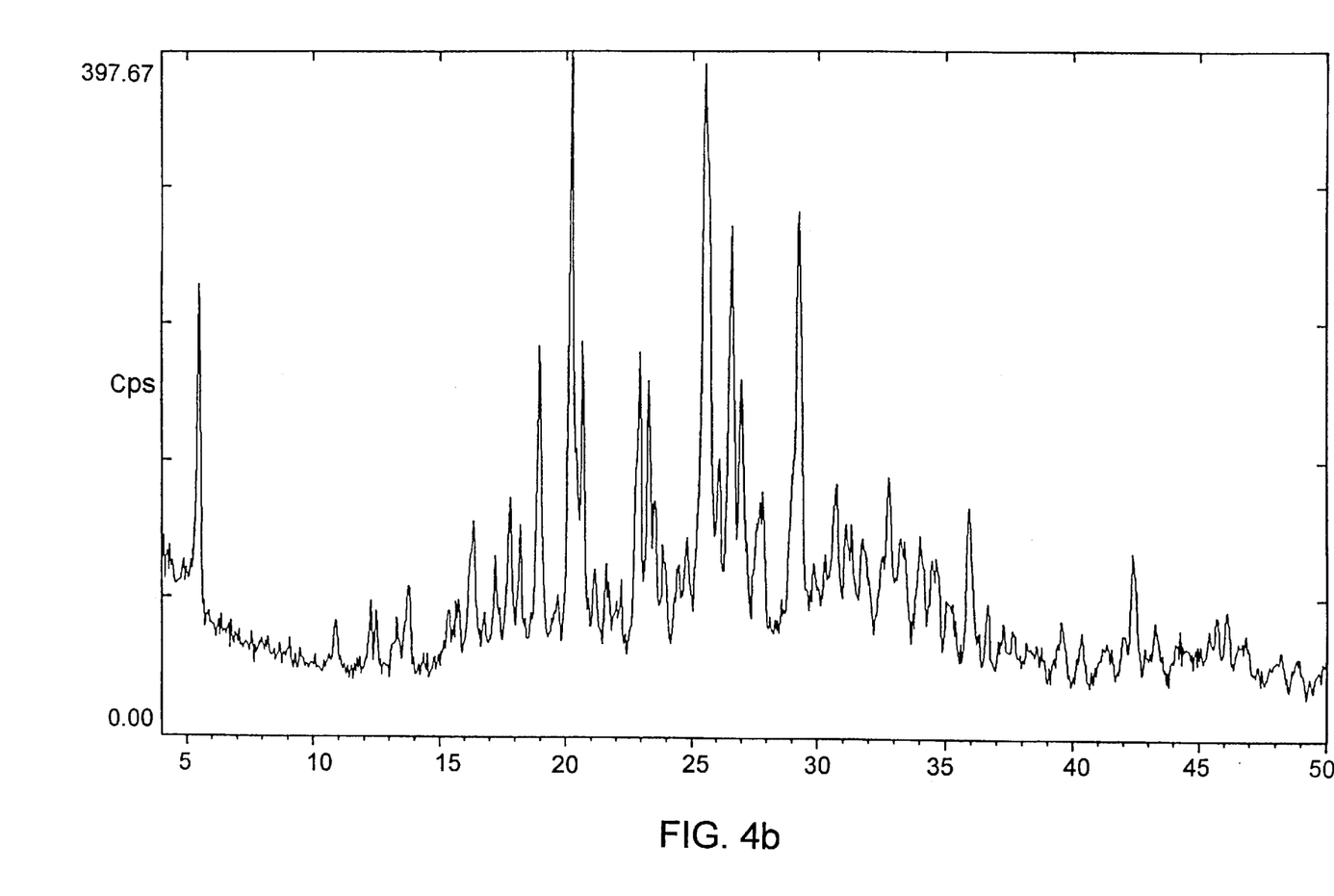
FIG. 4b shows the X-ray powder diffraction spectrum of the hydrated crystalline form of Lesopitron dihydrochloride, termed II-hydrate, obtained at $\lambda=1.5418$ Å, using a radiation source of $CuK_\alpha$, 40 kV and 30 mA (Siemens D-500 equipment).

The II-hydrate compound is also characterized by the following X-ray powder diffraction spectrum, where d is the spacing and $I/I_o$ is the relative intensity at $\lambda=1.5418$ Å, using a radiation source of $CuK_\alpha$, 40 kV and 30 mA (Siemens D-500 equipment) (see FIG. 4b):

| d (Å) | $I/I_o$ | d (Å) | $I/I_o$ |
|---|---|---|---|
| 16.16 | 65 | 4.10 | 25 |
| 8.13 | 17 | 3.90 | 40 |
| 7.28 | 14 | 3.88 | 56 |
| 7.21 | 19 | 3.82 | 52 |
| 7.10 | 18 | 3.78 | 34 |
| 6.65 | 17 | 3.48 | 98 |
| 6.43 | 21 | 3.47 | 83 |
| 5.63 | 19 | 3.41 | 39 |
| 5.47 | 25 | 3.35 | 74 |
| 5.42 | 31 | 3.30 | 52 |
| 5.14 | 26 | 3.08 | 38 |
| 4.98 | 35 | 3.05 | 76 |
| 4.87 | 31 | 2.91 | 37 |
| 4.68 | 56 | 2.73 | 38 |
| 4.39 | 100 | 2.63 | 29 |
| 4.35 | 42 | 2.59 | 26 |
| 4.29 | 57 | 2.50 | 33 |
| 4.20 | 24 | 2.13 | 27 |

The I-hydrate compound is prepared by hydration of polymorph I. Specifically, polymorph I is introduced in an air oven at room temperature. Air circulation is turned on generating a relative humidity equal to 80% or above. The product so obtained has a water content of between 3 and 6%. The I-hydrate compound reverts back to polymorph I by drying in an air oven at 40°–60° C.

Similarly, when polymorph II becomes hydrated, which is achieved by the generation of a 30–60% relative humidity, it yields the II-hydrate compound with a water content of between 1.5 and 2.5%. The II-hydrate compound reverts back to polymorph II by drying in an air oven at 40°–60° C.

The I-hydrate compound can be irreversibly obtained from the II-hydrate compound, by air circulation at room temperature. The kinetics of the process depend upon the atmospheric humidity.

The new I-hydrate compound has numerous advantages over the other forms I, II and II-hydrate, because it retains its specific physical properties in the manufacturing and storage conditions which are characteristic of pharmaceutical products, complying at all times with the required specifications of a pure product which has to be formulated. Indeed, during the storage of the product prior to the manufacture of the pharmaceutical speciality, the I-hydrate form is more stable than the other three compounds mentioned, which are hygroscopic and therefore absorb humidity. The smaller tendency of the I-hydrate compound towards hygroscopicity is very important, because the accuracy in the weighing of the product for the manufacture of tablets, would be affected by the humidity absorbed from the air, and constant analysis would be necessary to ensure the usage of the adequate amount of the active ingredient. Precision in the preparation of tablets is a particularly critical factor because the drug is effective at very low doses.

While Lesopitron dihydrochloride is very useful in the treatment of anxiety and it exerts other pharmacological activities over the central nervous system, the I-hydrate compound of this invention has the additional advantages of its ease of manufacture, its suitability for more precise formulation processes and that it is far less hygroscopic, which results in a greater physical stability and in an easier analysis of the content of the active ingredient.

The compound Lesopitron dihydrochloride I-hydrate can be formulated for administration in the most convenient form. The invention includes within its scope the pharmaceutical compositions which contain the I-hydrate form adapted for its use in human medicine. Such compositions can be presented for their conventional use with the help of a pharmaceutically acceptable carrier or excipient. Oral administration is preferable, particularly in the form of tablets or capsules.

For oral administration, the pharmaceutical composition can be presented in the form of, for example, tablets, capsules, solutions, syrups or suspensions prepared by conventional methods using pharmaceutically acceptable excipients.

A convenient daily dosification regime of the I-hydrate form of Lesopitron dihydrochloride, will be comprised between 5 and 100 mg/day, as a function of the condition of the patient.

The invention also relates to the use of the new compounds (polymorphs I and II, I-hydrate and II-hydrate) in the elaboration of drugs which exhibit a pharmacological activity over the central nervous system, particularly an anxiolytic, tranquilizing and antidepressant activity, as well as in the elaboration of adequate drugs for the treatment of dyskinesias, parkinson and drug induced psychoses, in the treatment of cognitive functions, inhibition of the withdrawal symptoms, vomit and gastric secretion related problems.

Additionaly, the invention provides a method for the treatment of individuals with alterations of the central nervous system and which requires a drug which exhibits pharmacological activity over said central nervous system, particularly an anxiolytic, tranquilizing and antidepressant activity, which comprises treating said individuals with an effective amount of, at least, one of the new compounds (polymorphs I and II, I-hydrate and II-hydrate) provided by this invention.

The invention also provides a method for the treatment of individuals affected by dyskinesias, parkinson and drug induced psychoses, as well as for the treatment of cognitive functions, inhibition of the withdrawal symptoms, vomit and gastric secretion related problems, which comprises treating said individuals with an effective amount of, at least, one of the new compounds (polymorphs I and II, I-hydrate and II-hydrate) provided by this invention.

The present invention is illustrated by the following examples, but is not limited to the details thereof.

EXAMPLE 1

Crude Lesopitron dihydrochloride

A 250 L enamelled reactor was loaded with an isopropanolic solution (57 Kg) of Lesopitron (25.2 mol), and was cooled to 5°–10° C. Subsequently, 8.5 Kg of a solution of hydrochloric acid (58.3 mol) in isopropanol were added, keeping the temperature between 5° and 15° C. during the addition. After stirring the suspension for 30 minutes, the product was centrifuged and washed with isopropanol. The Lesopitron dihydrochloride was washed and then dried in an air oven at 40° C. for 15 hours, obtaining 9.7 Kg (98% yield) of the compound mentioned in the title.

EXAMPLE 2

Polymorph I of Lesopitron dihydrochloride

An enamelled reactor was loaded with 84 L of 99% ethanol and 9.7 Kg of Lesopitron dihydrochloride were added to it. The suspension was heated under reflux and, once complete solution was achieved, it was kept boiling for 15 minutes, after which it was slowly cooled to between 50°–55° C., temperature interval within which crystallization of the polymorph I of Lesopitron dihydrochloride was observed. The suspension was stirred at 50°–55° C. for 30 minutes further. It was then cooled to 0°–5° C. for a time period of approximately 2 hours and was kept for 1 additional hour at the same temperature. After centrifuging and washing the crystalline solid with 99% ethanol, it was dried in an air oven at 45° C. for 15 hours, obtaining 8.5 Kg (88% yield) of polymorph I.

EXAMPLE 3

Lesopitron dihydrochloride I-hydrate 8.5 Kg of polymorph I of Lesopitron dihydrochloride were introduced in an air oven at room tempearture. Air circulation was switched on generating a relative humidity equal to 80% or above, obtaining 8.9 Kg of the 1-hydrate compound.

EXAMPLE 4

Polymorph II of Lesopitron dihydrochloride

A suspension of 50 g of Lesopitron dihydrochloride (127 mmol) in 400 ml of 99% ethanol was heated under reflux. The solution obtained was kept boiling for 10 additional minutes. It was then cooled rapidly to 0°–5° C., crystallization being observed between 23° and 26° C. The suspension was kept stirring at 0°–5° C. for 1 more hour. After filtering and washing with 99% ethanol, the product obtained was dried in an air oven at 50° C. for 15–17 hours, obtaining 44 g (88% yield) of polymorph II.

EXAMPLE 5

Preparation of Lesopitron dihydrochloride I-hydrate from polymorph II via the II-hydrate 4 g (10,2 mmol) of polymorph II of Lesopitron dihydrochloride were exposed to ambient humidity at room temperature. After 45 minutes, 4.062 g of the II-hydrate compound were obtained.

The II-hydrate so obtained was introduced in an air oven at room temperature. Air circulation was switched on generating a relative humidity equal to 80% or above, obtaining 4.16 g of the 1-hydrate compound.

EXAMPLE 6

Preparation of polymorph I from polymorph II 2 g of polymorph II of Lesopitron dihydrochloride (5.1 mmol) were suspended in 14 ml of 99% ethanol. It was heated to 55° C., maintaining the suspension under these conditions for 5.5 hours. Subsequently, it was cooled to 25° C. in approximately 1 hour, keeping this temperature overnight. After filtering and washing with 99% ethanol, the solid obtained was dried in an air oven at 50° C. for 20 hours, obtaining 1.67 g (83.3% yield) of polymorph I.

We claim:

1. Polymorph I of Lesopitron dihydrochloride, characterized in that its infrared diffuse reflectance spectrum has the following major bands (cm$^{-1}$) (FIG. 1a):

| | |
|---|---|
| 1910 | 965 |
| 1804 | 950 |
| 1626 | 936 |
| 1544 | 918 |
| 1411 | 902 |
| 1251 | 869 |
| 1218 | 798 |
| 1190 | 793 |
| 1139 | 765 |
| 1129 | 748 |
| 1122 | 738 |
| 1089 | 651 |
| 1077 | 642 |
| 1059 | 629 |
| 1034 | 616 |
| 1019 | 564 |
| 1008 | 518 |
| 988 | 471 |
| 981 | 442 |
| 978 | | and by the following X-ray powder diffraction spectrum, where d is the spacing and $I/I_o$ is the relative intensity at $\lambda=1.5418$ Å, using a radiation source of $CuK_\alpha$, 40 kV and 30 mA (Siemens D-500 equipment) (see FIG. 1b):

| d (Å) | $I/I_o$ | d (Å) | $I/I_o$ |
|---|---|---|---|
| 16.15 | 21 | 3.47 | 18 |
| 14.96 | 8 | 3.42 | 9 |
| 6.70 | 7 | 3.37 | 9 |
| 6.47 | 9 | 3.35 | 11 |
| 5.79 | 6 | 3.31 | 9 |
| 5.41 | 11 | 3.22 | 7 |
| 4.98 | 13 | 3.21 | 7 |
| 4.52 | 8 | 3.07 | 6 |
| 4.39 | 100 | 3.04 | 7 |
| 4.34 | 18 | 2.99 | 7 |
| 4.24 | 9 | 2.92 | 11 |
| 3.79 | 17 | 2.75 | 8 |
| 3.72 | 7 | 2.70 | 8 |
| 3.64 | 8 | 2.68 | 7 |
| 3.59 | 7 | 2.63 | 7 |
| 3.49 | 22 | 2.50 | 10 |
| | | 2.13 | 8 |

2. A crystalline hydrated form of Lesopitron dihydrochloride, termed I-hydrate, characterized in that its infrared diffuse reflectance spectrum has the following major bands (cm$^{-1}$) (FIG. 3a):

| | |
|---|---|
| 1900 | 994 |
| 1797 | 983 |
| 1624 | 972 |
| 1548 | 952 |
| 1527 | 940 |
| 1415 | 921 |
| 1404 | 898 |
| 1249 | 883 |
| 1245 | 795 |
| 1220 | 765 |
| 1195 | 749 |
| 1189 | 736 |
| 1139 | 659 |
| 1123 | 641 |
| 1112 | 631 |
| 1084 | 619 |
| 1078 | 520 |
| 1057 | 471 |
| 1031 | 416 | and by the following X-ray powder diffraction spectrum, where d is the spacing and $I/I_o$ is the relative intensity at $\lambda=1.5418$ Å, using a radiation source of $CuK_\alpha$, 40 kV and 30 mA (Siemens D-500 equipment) (FIG. 3b):

| d (Å) | $I/I_o$ | d (Å) | $I/I_o$ |
|---|---|---|---|
| 15.98 | 15 | 3.40 | 2 |
| 8.75 | 2 | 3.37 | 5 |
| 6.71 | 5 | 3.35 | 9 |
| 6.46 | 2 | 3.31 | 2 |
| 5.77 | 2 | 3.21 | 3 |
| 5.41 | 3 | 3.07 | 3 |
| 4.98 | 3 | 3.03 | 2 |
| 4.38 | 100 | 2.99 | 6 |
| 4.01 | 3 | 2.92 | 10 |
| 3.81 | 3 | 2.75 | 3 |
| 3.77 | 7 | 2.73 | 4 |
| 3.71 | 3 | 2.69 | 4 |
| 3.64 | 5 | 2.68 | 4 |
| 3.58 | 2 | 2.63 | 4 |
| 3.49 | 4 | 2.50 | 4 |
| 3.47 | 5 | 2.13 | 6 | having a water content between 3 and 6%.

3. Polymorph II of Lesopitron dihydrochloride, characterized in that its infrared diffuse reflectance spectrum has the following major bands (cm$^{-1}$) (FIG. 2a):

| | |
|---|---|
| 1913 | 989 |
| 1906 | 976 |
| 1799 | 966 |
| 1623 | 952 |
| 1588 | 917 |
| 1544 | 901 |
| 1538 | 878 |
| 1409 | 861 |
| 1248 | 796 |
| 1242 | 789 |
| 1220 | 765 |
| 1195 | 748 |
| 1136 | 651 |
| 1123 | 639 |
| 1085 | 635 |
| 1076 | 618 |
| 1061 | 558 |
| 1041 | 516 |
| 1031 | 510 |
| 1015 | 470 |
| 1011 | | and by the following X-ray powder diffraction spectrum, where d is the spacing and $I/I_o$ is the relative intensity at $\lambda=1.5418$ Å, using a radiation source of $CuK_\alpha$, 40 kV and 30 mA (Siemens D-500 equipment) (FIG. 2b):

| d (Å) | $I/I_o$ | d (Å) | $I/I_o$ |
|---|---|---|---|
| 16.22 | 57 | 4.11 | 25 |
| 14.95 | 38 | 3.90 | 60 |
| 8.15 | 32 | 3.88 | 85 |
| 7.24 | 40 | 3.83 | 76 |
| 7.10 | 37 | 3.78 | 33 |
| 6.68 | 36 | 3.49 | 98 |
| 6.46 | 29 | 3.47 | 100 |
| 5.65 | 29 | 3.42 | 31 |
| 5.45 | 37 | 3.35 | 90 |
| 5.42 | 27 | 3.30 | 45 |
| 5.14 | 35 | 3.05 | 97 |
| 4.98 | 28 | 2.91 | 31 |
| 4.88 | 46 | 2.73 | 27 |
| 4.69 | 96 | 2.63 | 24 |
| 4.39 | 89 | 2.59 | 27 |
| 4.30 | 78 | 2.50 | 25 |
| 4.21 | 28 | 2.13 | 18 |

4. A crystalline hydrated form of Lesopitron dihydrochloride, termed II-hydrate, characterized in that its infrared diffuse reflectance spectrum has the following major bands (cm$^{-1}$) (FIG. 4a):

| | |
|------|-----|
| 1902 | 971 |
| 1798 | 952 |
| 1621 | 940 |
| 1549 | 925 |
| 1537 | 917 |
| 1411 | 898 |
| 1404 | 881 |
| 1243 | 861 |
| 1219 | 790 |
| 1195 | 765 |
| 1189 | 749 |
| 1137 | 734 |
| 1123 | 659 |
| 1112 | 654 |
| 1087 | 639 |
| 1077 | 634 |
| 1057 | 618 |
| 1041 | 558 |
| 1029 | 517 |
| 1016 | 512 |
| 994  | 470 |
| 985  |     | and by the following X-ray powder diffraction spectrum, where d is the spacing and I/Io is the relative intensity at λ=1.5418 Å, using a radiation source of CuK$_\alpha$, 40 kV and 30 mA (Siemens D-500 equipment) (FIG. 4b):

| d (Å) | I/I$_o$ | d (Å) | I/I$_o$ |
|-------|---------|-------|---------|
| 16.16 | 65  | 4.10 | 25 |
| 8.13  | 17  | 3.90 | 40 |
| 7.28  | 14  | 3.88 | 56 |
| 7.21  | 19  | 3.82 | 52 |
| 7.10  | 18  | 3.78 | 34 |
| 6.65  | 17  | 3.48 | 98 |
| 6.43  | 21  | 3.47 | 83 |
| 5.63  | 19  | 3.41 | 39 |
| 5.47  | 25  | 3.35 | 74 |
| 5.42  | 31  | 3.30 | 52 |
| 5.14  | 26  | 3.08 | 38 |
| 4.98  | 35  | 3.05 | 76 |
| 4.87  | 31  | 2.91 | 37 |
| 4.68  | 56  | 2.73 | 38 |
| 4.39  | 100 | 2.63 | 29 |
| 4.35  | 42  | 2.59 | 26 |
| 4.29  | 57  | 2.50 | 33 |
| 4.20  | 24  | 2.13 | 27 | having a water content between 1.5 and 2.5%.

5. Process for the preparation of polymorph I of Lesopitron dihydrochloride according to claim 1, characterized in that a solution of Lesopitron dihydrochloride in a 1 to 4 carbon atom aliphatic alcohol, mono or polyhydroxilated, at the reflux temperature, is slowly cooled to 50°–55° C., bringing about crystallization; slow cooling is continued to 0°–5° C.; the crystalline mass is filtered, and the polymorph I of Lesopitron dihydrochloride so obtained is dried at 45° C.

6. Process according to claim 5, characterized in that said aliphatic alcohol is ethanol.

7. Process for the preparation of a crystalline hydrated form of Lesopitron dihydrochloride, termed I-hydrate, according to claim 2, characterized in that polymorph I, having an infrared diffuse reflectance spectrum having the, the following major bands (cm$^{-1}$) (FIG. 1a):

| | |
|------|-----|
| 1910 | 965 |
| 1804 | 950 |
| 1626 | 936 |
| 1544 | 918 |
| 1411 | 902 |
| 1251 | 869 |
| 1218 | 798 |
| 1190 | 793 |
| 1139 | 765 |
| 1129 | 748 |
| 1122 | 738 |
| 1089 | 651 |
| 1077 | 642 |
| 1059 | 629 |
| 1034 | 616 |
| 1019 | 564 |
| 1008 | 518 |
| 988  | 471 |
| 981  | 442 |
| 978  |     | and the following X-ray powder diffraction spectrum where d is the spacing and I/I$_o$ is the relative intensity at λ=1.5418 Å, using a radiation source of CuK$_\alpha$, 40 kV and 30 mA (Siemens D-500 equipment) (see FIG. 1b):

| d (Å) | I/I$_o$ | d (Å) | I/I$_o$ |
|-------|---------|-------|---------|
| 16.15 | 21  | 3.47 | 18 |
| 14.96 | 8   | 3.42 | 9  |
| 6.70  | 7   | 3.37 | 9  |
| 6.47  | 9   | 3.35 | 11 |
| 5.79  | 6   | 3.31 | 9  |
| 5.41  | 11  | 3.22 | 7  |
| 4.98  | 13  | 3.21 | 7  |
| 4.52  | 8   | 3.07 | 6  |
| 4.39  | 100 | 3.04 | 7  |
| 4.34  | 18  | 2.99 | 7  |
| 4.24  | 9   | 2.92 | 11 |
| 3.79  | 17  | 2.75 | 8  |
| 3.72  | 7   | 2.70 | 8  |
| 3.64  | 8   | 2.68 | 7  |
| 3.59  | 7   | 2.63 | 7  |
| 3.49  | 22  | 2.50 | 10 |
|       |     | 2.13 | 8  | is introduced in an air oven at room temperature, and air circulation is switched on in order to generate at least an 80% relative humidity, obtaining the desired I-hydrate compound.

8. Process for the preparation of polymorph II of Lesopitron dihydrochloride according to claim 3, characterized in that a solution of Lesopitron dihydrochloride in a 1 to 4 carbon atom aliphatic alcohol, mono or polyhydroxilated, at the reflux temperature, is rapidly cooled to 0°–5° C., bringing about crystallization at 20°–30° C.; the crystalline mass is filtered and the polymorph II of Lesopitron dihydrochloride so obtained is dried at 50° C.

9. Process according to claim 8, characterized in that said aliphatic alcohol is ethanol.

10. Process for the preparation of a crystalline hydrated form of Lesopitron dihydrochloride, termed II-hydrate, according to claim 4, characterized in that polymorph II, of Lesopitron dihydrochloride, whose infrared diffuse reflectance spectrum has the following major bands (cm$^{-1}$) (FIG. 2a):

| | |
|------|-----|
| 1913 | 989 |
| 1906 | 976 |

-continued

| | |
|---|---|
| 1799 | 966 |
| 1623 | 952 |
| 1588 | 917 |
| 1544 | 901 |
| 1538 | 878 |
| 1409 | 861 |
| 1248 | 796 |
| 1242 | 789 |
| 1220 | 765 |
| 1195 | 748 |
| 1136 | 651 |
| 1123 | 639 |
| 1085 | 635 |
| 1076 | 618 |
| 1061 | 558 |
| 1041 | 516 |
| 1031 | 510 |
| 1015 | 470 |
| 1011 | | and whose X-ray powder diffraction spectrum is as follows where d is the spacing and $I/I_o$ is the relative intensity at $\lambda=1.5418$ Å, using a radiation source of $CuK_\alpha$, 40 kV and 30 mA (Siemens D-500 equipment) (FIG. 2b):

| d (Å) | $I/I_o$ | d (Å) | $I/I_o$ |
|---|---|---|---|
| 16.22 | 57 | 4.11 | 25 |
| 14.95 | 38 | 3.90 | 60 |
| 8.15 | 32 | 3.88 | 85 |
| 7.24 | 40 | 3.83 | 76 |
| 7.10 | 37 | 3.78 | 33 |
| 6.68 | 36 | 3.49 | 98 |
| 6.46 | 29 | 3.47 | 100 |
| 5.65 | 29 | 3.42 | 31 |
| 5.45 | 37 | 3.35 | 90 |
| 5.42 | 27 | 3.30 | 45 |
| 5.14 | 35 | 3.05 | 97 |
| 4.98 | 28 | 2.91 | 31 |
| 4.88 | 46 | 2.73 | 27 |
| 4.69 | 96 | 2.63 | 24 |
| 4.39 | 89 | 2.59 | 27 |
| 4.30 | 78 | 2.50 | 25 |
| 4.21 | 28 | 2.13 | 18 | is introduced in an air oven at room temperature, and air circulation is switched on in order to generate 30–60% relative humidity, obtaining the desired II-hydrate compound.

11. Process for the preparation of polymorph I of Lesopitron dihydrochloride according to claim 1, characterized in that polymorph II, of Lesopitron dihydrochloride, whose infrared diffuse reflectance spectrum has the following major bands (cm$^{-1}$) (FIG. 2a):

| | |
|---|---|
| 1913 | 989 |
| 1906 | 976 |
| 1799 | 966 |
| 1623 | 952 |
| 1588 | 917 |
| 1544 | 901 |
| 1538 | 878 |
| 1409 | 861 |
| 1248 | 796 |
| 1242 | 789 |
| 1220 | 765 |
| 1195 | 748 |
| 1136 | 651 |
| 1123 | 639 |
| 1085 | 635 |
| 1076 | 618 |
| 1061 | 558 |
| 1041 | 516 |
| 1031 | 510 |
| 1015 | 470 |
| 1011 | | and whose X-ray powder diffraction spectrum is as follows where d is the spacing and $I/I_o$ is the relative intensity at $\lambda=1.5418$ Å, using a radiation source of $CuK_\alpha$, 40 kV and 30 mA (Siemens D-500 equipment) (FIG. 2b):

| d (Å) | $I/I_o$ | d (Å) | $I/I_o$ |
|---|---|---|---|
| 16.22 | 57 | 4.11 | 25 |
| 14.95 | 38 | 3.90 | 60 |
| 8.15 | 32 | 3.88 | 85 |
| 7.24 | 40 | 3.83 | 76 |
| 7.10 | 37 | 3.78 | 33 |
| 6.68 | 36 | 3.49 | 98 |
| 6.46 | 29 | 3.47 | 100 |
| 5.65 | 29 | 3.42 | 31 |
| 5.45 | 37 | 3.35 | 90 |
| 5.42 | 27 | 3.30 | 45 |
| 5.14 | 35 | 3.05 | 97 |
| 4.98 | 28 | 2.91 | 31 |
| 4.88 | 46 | 2.73 | 27 |
| 4.69 | 96 | 2.63 | 24 |
| 4.39 | 89 | 2.59 | 27 |
| 4.30 | 78 | 2.50 | 25 |
| 4.21 | 28 | 2.13 | 18 | is suspended in a 1 to 4 carbon atom aliphatic alcohol, mono or polyhydroxilated, and is stirred at a temperature between 25° and 80° C. preferably at 55° C., for a time comprised between 4 and 24 hours, and it is subsequently cooled to 25° C. in approximately 1 hour, obtaining the desired polymorph I.

12. Process according to claim 11, characterized in that said aliphatic alcohol is ethanol.

13. Pharmaceutical tablet which comprises polymorph I of Lesopitron dihydrochloride according to claim 1, in combination with a pharmaceutically acceptable carrier.

14. Pharmaceutical tablet which comprises a hydrated form of Lesopitron dihydrochloride according to claim 2, in tablet with a pharmaceutically acceptable carrier.

15. Pharmaceutical tablet which comprises polymorph II of Lesopitron dihydrochloride according to claim 3, in combination with a pharmaceutically acceptable carrier.

16. Pharmaceutical tablet which comprises a hydrated form of Lesopitron dihydrochloride according to claim 4, in combination with a pharmaceutically acceptable carrier.

17. Method of treating a patient for disorders associated with the central nervous system, which comprises administering a therapeutically effective amount of a drug containing the polymorph I of Lesopitron dihydrochloride, a hydrated form of Lesopitron dihydrochloride termed I-hydrate, polymorph II of Lesopitron dihydrochloride or a hydrated form of Lesopitron dihydrochloride, termed II-hydrate.

18. Method of treating a patient, which comprises administering a drug which exhibits anxiolytic, tranquilizing and antidepressant activity, such drug containing the polymorph I of Lesopitron dihydrochloride, a hydrated form of Lesopitron dihydrochloride termed I-hydrate, polymorph II of Lesopitron dihydrochloride or a hydrated form of Lesopitron dihydrochloride, termed II-hydrate.

19. Method of treating a patient, in need of a treatment against diskinesias, Parkinsonism, drug-induced psychoses, treatment of cognitive functions, inhibition of the withdrawal symptoms, vomit and gastric secretion related problems, which comprises administering a therapeutically effective amount of drug containing the polymorph I of Lesopitron dihydrochloride, a hydrated form of Lesopitron dihydrochloride termed I-hydrate, polymorph II of Lesopitron dihydrochloride or a hydrated form of Lesopitron dihydrochloride, termed II-hydrate.

* * * * *